US011946872B2

(12) United States Patent
Latour et al.

(10) Patent No.: US 11,946,872 B2
(45) Date of Patent: *Apr. 2, 2024

(54) COUPON DESIGN FOR ENHANCED COLOR SENSITIVITY FOR COLORIMETRIC-BASED CHEMICAL ANALYSIS OF LIQUIDS

(71) Applicant: Clemson University Research Foundation, Clemson, SC (US)

(72) Inventors: Robert A. Latour, Clemson, SC (US); George Chumanov, Clemson, SC (US); Alexandra Cholewczynski, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/882,931

(22) Filed: Aug. 8, 2022

(65) Prior Publication Data

US 2022/0397535 A1 Dec. 15, 2022

Related U.S. Application Data

(62) Division of application No. 16/639,436, filed as application No. PCT/US2018/049347 on Sep. 4, 2018, now Pat. No. 11,415,523.

(Continued)

(51) Int. Cl.
*G01N 33/52* (2006.01)
*G01N 21/78* (2006.01)
(Continued)

(52) U.S. Cl.
CPC ........... *G01N 21/78* (2013.01); *G01N 33/493* (2013.01); *G01N 33/523* (2013.01); *G01N 33/70* (2013.01); *G01N 2021/7766* (2013.01)

(58) Field of Classification Search
CPC ......... G01N 21/645; G01N 2201/0221; G01N 21/00; G01N 2201/062; G01N 21/8483;
(Continued)

(56) References Cited

U.S. PATENT DOCUMENTS 3,048,475 A * 8/1962 Rupe .................... G01N 33/64
436/128
3,954,412 A * 5/1976 Ogawa .................. G01N 33/64
436/128

(Continued)

OTHER PUBLICATIONS

ISA/US; ISR and Written Opinion prepared for PCT/US2018/049347; dated Jan. 4, 2019.

*Primary Examiner* — Shogo Sasaki
(74) *Attorney, Agent, or Firm* — Joseph T. Guy; Patent Filing Specialist Inc.

(57) ABSTRACT

A system for monitoring an analyte concentration in liquid is provided. The system includes a coupon comprising an absorbent body with a window through the absorbent body wherein the liquid is maintained in said window by capillary action and surface tension. A reactant is in the absorbent body wherein the reactant is capable of diffusing into the window to react with an analyte in the liquid, or the reactant is able to react with the analyte within the coupon itself, with color-indicating by-products of the reaction diffusing into the window, wherein the analyte is present in an analyte concentration, to form a reactant with a color wherein the color has an intensity which correlates to the analyte concentration. A light source is provided which is capable of passing light into the window wherein the light is attenuated by the color proportional to the analyte concentration to form attenuated light. A detector is provided which is capable measuring an intensity of the attenuated light.

(Continued)

Alternatively, the color change can be read by eye and compared to a color chart relating the color to an analyte concentration.

19 Claims, 4 Drawing Sheets

Related U.S. Application Data

(60) Provisional application No. 62/554,873, filed on Sep. 6, 2017.

(51) Int. Cl.
*G01N 33/493* (2006.01)
*G01N 33/70* (2006.01)
*G01N 21/77* (2006.01)

(58) Field of Classification Search
CPC ......... G01N 33/523; G01N 2021/7796; G01N 33/70; G01N 2021/7766; G01N 21/293; G01N 33/493; G01N 21/78
See application file for complete search history.

(56) References Cited

U.S. PATENT DOCUMENTS

| | | | | |
|---|---|---|---|---|
| 4,954,435 | A * | 9/1990 | Krauth | G01N 21/17 436/805 |
| 5,104,619 | A * | 4/1992 | de Castro | G01N 33/528 422/422 |
| 6,541,269 | B1 | 4/2003 | Ramana et al. | |
| 9,194,807 | B2 * | 11/2015 | Song | C12Q 1/44 |
| 2002/0086435 | A1 * | 7/2002 | Fernandez Decastro | G01N 33/526 436/166 |
| 2002/0168776 | A1 | 11/2002 | Cizdziel et al. | |
| 2005/0109951 | A1 * | 5/2005 | Fish | G01N 21/64 250/461.1 |
| 2008/0013092 | A1 * | 1/2008 | Maltezos | G01N 21/6456 356/417 |
| 2010/0315644 | A1 * | 12/2010 | Egan | G01N 21/84 356/445 |
| 2014/0128596 | A1 * | 5/2014 | Zuk | G01N 21/645 536/123.1 |
| 2016/0077037 | A1 | 3/2016 | Cha et al. | |
| 2020/0283583 | A1 * | 9/2020 | Leroux | G01N 33/689 |

* cited by examiner

COUPON DESIGN FOR ENHANCED COLOR SENSITIVITY FOR COLORIMETRIC-BASED CHEMICAL ANALYSIS OF LIQUIDS

CROSS-REFERENCE TO RELATED APPLICATIONS

The present application is a divisional application of pending U.S. patent application Ser. No. 16/639,436 filed Feb. 14, 2020; now U.S. Pat. No. 11,415,523 issued Aug. 16, 2022; which is a 35 USC § 371 filing of expired PCT/US18/49347 filed Sep. 4, 2018 which, in turn, claims priority to expired U.S. Provisional Patent Application No. 62/554,873 filed Sep. 6, 2017 the entire contents of which are all incorporated by reference herein.

FIELD OF THE INVENTION

The present invention is related to a coupon which is particularly suited for use in colorimetric-based chemical analysis of liquids. More particularly, the present invention is related to a coupon design which provides for improved sensitivity and uniformity in colorimetric-based chemical analysis due to an increased optical path length for light transmission through a developed liquid column with minimal structural barriers.

BACKGROUND

Colorimetric-based chemical analysis is a widely used technique for many chemical assays including, biologically relevant analytes, tap water quality testing, industrial and environmental testing, pool and spa testing and the like as set forth in U.S. Pat. No. 6,541,269 which is incorporated herein by reference. Colorimetric based chemical analysis can be used for a variety of analytes including metals, such as copper or iron, inorganics, such as free chlorine or total chlorine, and biologically relevant components.

Indicators useful for evaluating chlorine include benzidine-type chromogens, diaminothiobenzo-phenone-type chromogens, and azine compounds such as syringaldazine and vanillinazine. Indicators useful for evaluating iron include 2,4,6-tri(2-pyridyl)-1,3,5-triazine (TPTZ), and indicators useful for evaluating copper include 5-(4-dimethylaminobenzylidene)rhodanine.

Benzidine indicators are especially useful for evaluating free chlorine, including the 3,3',5,5'-tetraalkylbenzidines, wherein alkyl is C1-C3 alkyl, in particular methyl and ethyl, and 3,3',5,5'-tetramethyl-benzidine (TMB) is particularly preferred. Other benzidines within the foregoing formula, include 3,3'-dimethyl, 5,5'-diethyl benzidine and 3,3',5,5'-tetraethylbenzidine. The four alkyl groups may be the same or different. To prevent leaching from the carrier in a water-based sample, the free base form is typically preferred.

Diaminothiobenzophenone indicators are especially useful for evaluating total chlorine, including the 4,4'- bis(dialkylamino)thiobenzophenones, wherein alkyl is C1-C3 alkyl, in particular methyl and ethyl, and 4,4'-bis(dimethylamino)thiobenzophenone is particularly preferred.

Particularly preferred biological samples are described in U.S. Pat. Nos. 5,563,042 and 3,298,789, both of which are incorporated herein by reference, wherein the analysis of blood samples is described. Fresh, whole blood (typically 20-40 µl) is placed on an ethylcellulose-coated reagent pad containing an enzyme system having glucose oxidase and peroxidase activity. The enzyme system reacts with glucose and releases hydrogen peroxide. The pad also contains an indicator which reacts with the hydrogen peroxide in the presence of peroxidase to give a color proportional in intensity to the sample's glucose level.

A particular disease which is difficult to test for is phenylketonuria (PKU) which is a rare metabolic disorder that occurs in the USA at a frequency of about 1 in 10,000 children. PKU is caused by a genetic defect in the liver enzyme phenylalanine hydroxylase which converts the amino acid phenylalanine (Phe) to tyrosine. If untreated, Phe levels in the blood stream rise to toxic levels which can lead to irreversible brain damage and mental retardation within a few months after birth. For this reason, newborns are screened in the United States for the presence of PKU. If diagnosed, treatment involves strict metabolic control using a low-Phe diet combined with special medical foods preferably initiated within the first seven days of life and followed throughout life. If properly controlled, normal health and development can be expected. Current guidelines recommend that blood plasma levels be maintained between 120-360 µM (2.0-6.0 mg/dL) for PKU patients of all ages.

Phe levels are typically monitored by dried-blood-spot samples taken at home and mailed to a participating laboratory for analysis. Clinical recommendations are for blood Phe levels to be checked once per week for the first five years of life and at least one a month thereafter. Women of childbearing age with PKU must be especially careful to maintain low blood Phe levels which is preferably monitored by weekly blood monitoring prior to conception, and throughout pregnancy, or birth defects can result even if the fetus does not have PKU.

Reducing the impact of PKU has been exasperated by the fact that a blood test for Phe typically requires 5 to 10 days for results to be returned to the patient or the patient's family, making it difficult to control blood Phe since any dietary impact may not be determined for 5 to 10 days and, even then, long after any dietary perturbation. The lag-time between sampling and obtaining the results can cause substantial problems in the dietary regulation of blood Phe levels thereby making it very difficult to maintain Phe in the desired level on a daily basis.

In about 1934 it was discovered that the condition of PKU resulted in abnormally high levels of phenylpyruvic acid (PPA) in urine, which is the result of the liver's inability to properly metabolize Phe. This realization eventually led to the development of a colorimetric urine test for PPA in the late 1950s as the first newborn screening test for PKU. The test involved a reaction with ferric chloride and the reaction was used in a standard test utilizing ferric-chloride-impregnated test strips. Though somewhat beneficial, the test had poor sensitivity with a lower range of detection associated with blood Phe levels of about 900 µM. Therefore the test was only suitable for the initial detection of PKU but the test was not suitable for routine monitoring of blood Phe levels once they were brought under dietary control to be within the therapeutically recommended range of between 120-360 µM.

There has been a long-standing desire for improved methods and systems for colorimetric-based measurement of analytes. There is a particular need for a more immediate test for blood Phe levels and preferably an in-home, or point-of-care, Phe-monitoring system to allow patients the opportunity to engage in more time-responsive maintenance of blood Phe levels. Efforts to achieve an at-home blood test have thus far not been successful. A urine based test is provided herein wherein a novel coupon provides for a convenient method of sampling and monitoring of blood Phe levels for individuals with PKU.

SUMMARY OF THE INVENTION

It is an object of the invention to provide an improved method for colorimetric-based chemical analysis.

It is a particular object of the invention to provide a test for analytes in a liquid using colorimetric-based chemical analysis.

It is a particular object of the invention to provide a urine test for blood Phe concentration suitable for diagnosing or monitoring of PKU.

A particular feature of the invention is the ability to provide an at-home, or point-of-care, measurement of PPA and creatinine (CRE) concentration in urine simply and at a low cost. CRE measurement is used as the standard method to normalize urine test results for dilution effects due to the degree of patient hydration.

These and other embodiments, as will be realized, are provided in a system for monitoring an analyte concentration in a liquid sample. The system includes a coupon comprising an absorbent body with a window through the absorbent body wherein the liquid is maintained in the window by a combination of capillary action and liquid surface tension. A reactant is in the absorbent body wherein the reactant, and/or reaction products caused by the reactant, are capable of diffusing into the window to react with an analyte in the test liquid, or reacted analyte from the absorbent body itself is capable of mixing with the analyte liquid in the window by diffusion or convection, wherein the analyte is present in an analyte concentration, to form a reactant with a color wherein the color has an intensity that correlates to the analyte concentration. A light source is provided which is capable of passing a light beam into the window wherein the light is attenuated by the color proportional to the analyte concentration to form attenuated light. A detector is provided which is capable of measuring an intensity of the attenuated light. Alternatively, the color response of the coupon can simply be viewed by eye under ambient lighting conditions, with the color response compared to a color chart indicating the relationship between the color and the concentration of the designated analyte.

Yet another embodiment is provided in a method for monitoring an analyte concentration in liquid comprising: providing a coupon comprising an absorbent body with a window through the absorbent body; placing the test liquid in the window; allowing the reactant in the absorbent body to diffuse into the window to react with an analyte in the test liquid, or reacted analyte from the absorbent body itself, to form a color wherein the color has an intensity which correlates to the analyte concentration; passing a light beam into the window wherein the light is attenuated by the color proportional to the analyte concentration to form attenuated light; and measuring an intensity of the attenuated light. Alternatively, the color response of the coupon can simply be viewed by eye under ambient lighting conditions, with the color response compared to a color chart indicating the relationship between the color and the concentration of the designated analyte.

Yet another embodiment is provided in a system for controlling phenylketonuria. The system includes a coupon comprising an absorbent body with a window through the absorbent body. A reactant is in the absorbent body wherein the reactant, and/or reaction products caused by the reactant, are capable of diffusing into the window to react with PPA or CRE in urine contained in the window, or reacted PPA or CRE from the absorbent body itself is capable of mixing with the liquid in the window by diffusion or convection, to form a color wherein the color has an intensity which correlates to the phenylpyruvic acid or creatinine concentration. A light source is provided which is capable of passing a light beam into the window wherein the light is attenuated by the color proportional to the phenylpyruvic acid or creatinine concentration to form attenuated light. A detector is provided which is capable of measuring an intensity of attenuated light. Alternatively, the color response of the coupon can simply be viewed by eye under ambient lighting conditions, with the color response compared to a color chart indicating the relationship between the color and the concentration of the designated analyte.

DESCRIPTION

Figure 1:
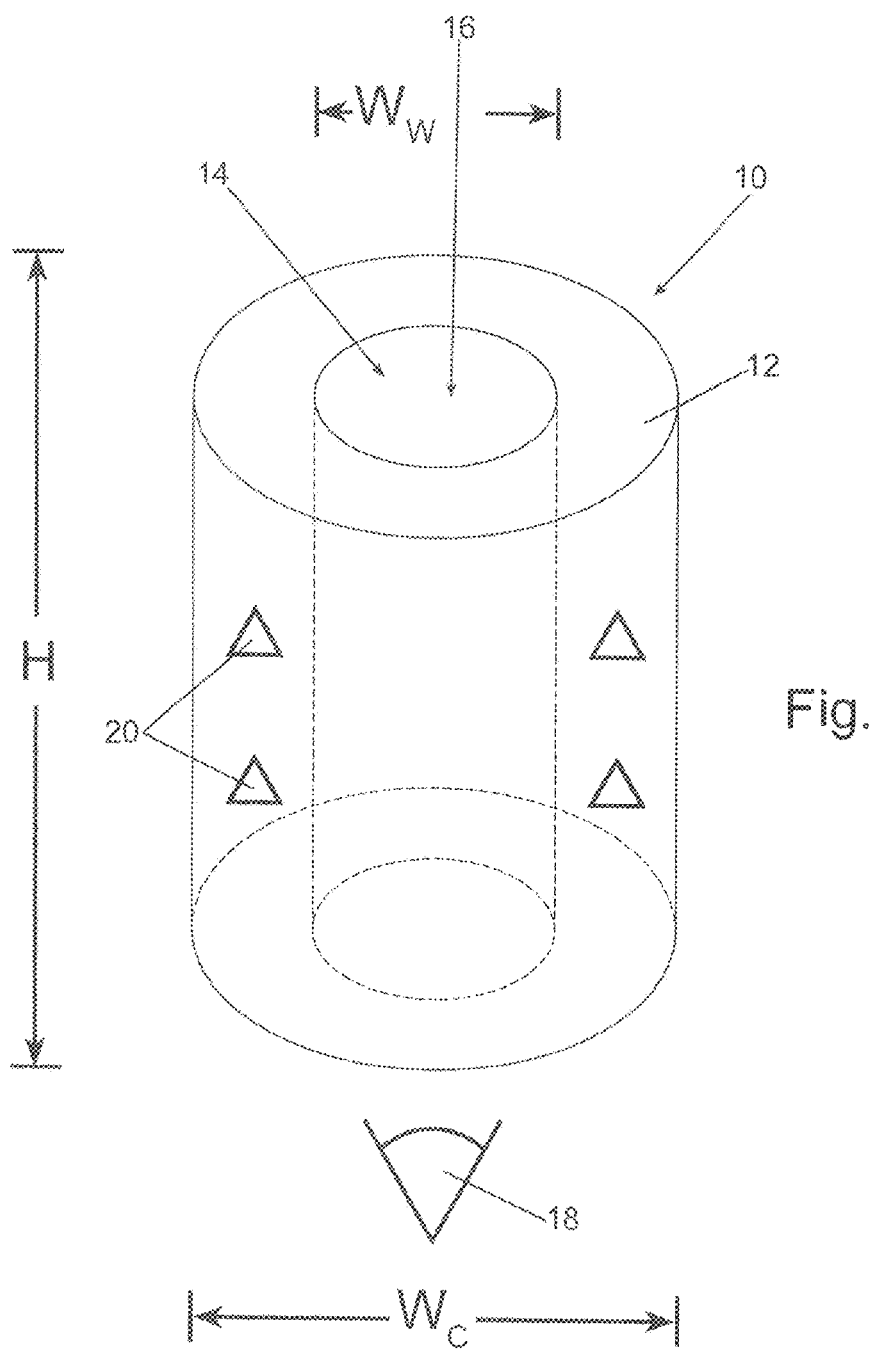
FIG. 1 is a schematic representation of an embodiment of the invention.

The present invention is directed to a coupon, and method, for detecting analytes in a liquid sample by colorimetric processes with improved precision. More specifically, the present invention is directed to a coupon, and method, for detecting PPA and CRE in urine by colorimetric processes with improved precision. Even more specifically, the present invention is directed to a coupon, and method, wherein PPA and CRE can be measured in urine thereby correlating with Phe blood levels with improved accuracy, and improved precision, in a significantly reduced time and at a low cost thereby providing an at-home, or point-of-care, method for determining Phe blood levels for improved dietary control for patients with PKU.

The present invention provides an improved colorimetric technique, based in one embodiment, on the reaction of an appropriate color-indicating compound with phenylpyruvic acid or creatinine, wherein a coupon is provided which allows for an increase in the path length of light transmission, preferably with minimal structural interference thereby increasing the amount of reactant in the light path and subsequently increased sensitivity.

The colorimetric indicator, or reactant, may be organic or inorganic, but in any event will be suitable for the analyte to be measured. Accordingly, the indicator and other test additives may advantageously be substantially soluble or insoluble in the liquid being analyzed.

The coupon design significantly enhances the sensitivity and uniformity of color change upon exposure to a target analyte in a test solution compared to conventional color-indicating substrates. This coupon consists of an absorbent outer layer with the outside dimension ranging from a few millimeters to a few tens of millimeters and up to several millimeters thick or more. The coupons can be made out of a layer of absorbent material, such as cotton or cellulose (e.g., paper), with a central hole up to several millimeters in diameter (or width) formed perpendicular to the surface plane of the coupon. The coupons can also be made of materials that are translucent or opaque such to transmit light, not transmit light, or transmit light to a limited degree. Such coupons can be made by punching out disks of thick blotting filter paper, which may be pre- or post-treated to alter their light transmitting characteristics, followed by using a hole punch to create the inner open hole. Such coupons can also be made by winding a thin sheet of absorbent material that is capable of wicking liquids (e.g., paper towel) around a cylindrical mandrel, which may be pre- or post-treated to alter their light transmitting characteristics, followed by the removal of the mandrel, securing the rolled-up material to prevent it from unwinding (i.e., with an outer wrap or adhesive), and slicing the resulting cylinder to obtain a desired coupon thickness. In this second instance, the dimension of the internal hole will be determined by the diameter of the mandrel after its removal. By this design, when exposed to a test liquid, the hole (or cavity) is capable of supporting a column of liquid by a combination of liquid surface tension and the wicking properties of the surrounding absorbent coupon material. It is this cavity where the enhancement of the color change is observed when compared to the color change in the bulk of the coupon. It is important to emphasize that traditional and commercially available colorimetric tests focus on color changes that take place for a film of color-indicating reagent formed on a substrate material or impregnated in the bulk of a porous medium without enhancement by the entrapment of a column of pure liquid. Contrary to conventional coupons for colorimetric analyses, the invention focuses on providing significantly enhanced color change and enhanced color uniformity that take place in the liquid column held within the internal cavity of the coupon. The role of the surrounding porous medium is to rapidly wick the test liquid up into the coupon and support a column of liquid within the coupon by surface tension. It is also to contain the color-indicating reagent that the coupon is impregnated with that will cause a uniform color in the supported column of test liquid as the color indicating agent reacts with the test liquid that is wicked up into the absorbent material of the coupon to cause the color change and subsequently diffuse into and equilibrate with the supported column of liquid to likewise cause it to change color in proportion to the concentration of the analyte that is being tested for. This method essentially enables chemical spectroscopy to be conducted for the quantitative measurement of the concentration of targeted analytes without the use of expensive laboratory spectroscopy equipment, thus facilitating its use in the field or at home for chemical analysis. Alternatively, the color response of the coupon can be read using a laboratory spectroscopy instrument.

An embodiment of the invention can be demonstrated in a urine analysis test to quantitatively determine the concentration of PPA and CRE in urine. PPA is a metabolic byproduct of unusually high concentrations of the amino acid phenylalanine (Phe) in the blood stream, which is important for the dietary management of a rare genetic disease called phenylalanine hydroxylase (PAH) deficiency, or also known as phenylketonuria (PKU). For the measurement of PPA in urine (or simulated urine substitutes), a ferric chloride compound, derived from a 1950s product called Phenistix, has been used, which is dried on various absorbent test substrates to produce color-indicating test coupons. When exposed to a test liquid containing PPA, this compound changes from a clear or light yellowish-orange color to a greenish-blue color in proportion to the concentration of PPA in the test liquid. The greatest sensitivity and uniformity to PPA (i.e., darkest and most uniform color change for a given concentration of PPA in the test liquid), is provided by a liquid solution of the Phenistix compound.

To demonstrate the invention a substrate, or test coupon, can be formed from a very absorbent material, with a thickness greater than about 2 mm, and with a 1-3 mm diameter window formed with its central axis normal to the surface plane of the coupon. The test coupon is impregnated with the reactant, which is a color-indicating agent, dried, and then immersed in the liquid to be tested, removed, and placed on a relatively hydrophobic surface. Alternatively, the test fluid can be poured over the coupon. The coupon then retains a column of liquid within the window due to the absorbent material rapidly wicking the test liquid into the coupon combined with the surface tension of this wicked liquid supporting the column of pure liquid within the central cavity. The fluid in the supported column of liquid then exchanges with the liquid in the absorbent coupon by diffusion causing it to rapidly equilibrate and change color in response to the concentration of the analyte in the test solution. The intensity of color change provided by the color-indicating coupons is as strong and uniformly presented as in a pure liquid-solution.

The invention will be described with reference to the figures forming an integral non-limiting component of the description. Throughout the description similar elements will be numbered accordingly.

Figure 2:
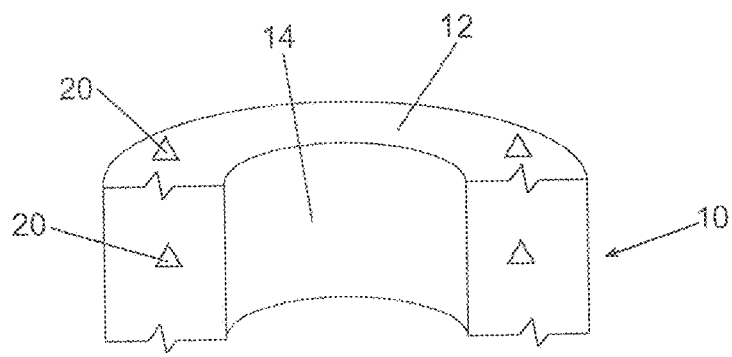
FIG. 2 is a schematic representation of an embodiment of the invention.

An embodiment of the invention will be described with reference to FIGS. 1 and 2. A coupon is illustrated in top perspective view in FIG. 1 and partial cut-away top perspective view in FIG. 2. In FIGS. 1 and 2 the coupon, generally represented at 10, comprises an absorbent body, 12, with a preferably centrally located window, 14, extending through the coupon within which the sample to be measured will reside and through which the colorimetric results will be read as will be realized from further discussion. At least one reactant, 20, preferably ferric salt for PPA measurement, is embedded in the absorbent body. Upon filling the window with a sample to be tested, preferably urine comprising at least one analyte, the reactant migrates into the sample wherein a reaction occurs between the reactant and analyte resulting in a color with an intensity correlated to the analyte concentration in the sample. A particular feature of the invention is the size of the coupon which is chosen such that the height (H) is sufficiently long to achieve sufficient color intensity such that the light, 16, is attenuated sufficiently to monitor a loss of light intensity at a detector, 18, which can be a light-detecting instrument or detected by eye, preferable a human eye, for optical comparison with a standard such as a color chart, color density chart or optical density chart comprising a control color or control density wherein the control color or control density is correlated to analyte concentration. Although the detector is illustrated opposite of the light source in FIG. 1 for transmission spectroscopy, it can also be placed on the same side of the coupon as the light source to perform reflectance spectroscopy.

The coupon can similarly be applied for any type of colorimetric analysis for the determination of a targeted analyte in a liquid sample where a color-indicating chemical is deposited within the absorbent portion of the coupon. This coupon design provides enhanced sensitivity and uniformity to a designated analyte compared to similar coupon or test strip designs without the window for retaining a liquid column of fluid within the coupon.

The coupon comprises an absorbent outer layer surrounding an inner window with the absorbent outer layer being thick enough to support a column of the test liquid within the window. Accordingly, instead of a circular window the surrounding outer absorbent material and the inner cavity could be different shapes and windows do not need to be centered or oriented normal to the coupon surface plane but could be offset and/or angled from the central axis of the coupon. For example, the absorbent material could be in the form of an absorbent sheet of material with or without a series of impermeable boundaries formed within the sheet to separate various compartments, with each compartment having its own window. The absorbent material of separate compartments could then be impregnated with either the same or different color-indicating reagents. The whole absorbent sheet could then be wetted with the same test liquid to perform multiple analyses at once for the same test liquid with each separate compartment providing its own colorimetric response, or different test liquids could be added to different compartments to analyze multiple test liquids at one time.

Ferric salts for the colorimetric measurement of PPA concentration are chosen to be stable to ambient conditions, easily absorbed into the coupon and capable of diffusing from the coupon to the sample in a reasonable period of time such as less than five minutes. Preferred ferric salts include ferric ammonium sulfate, ferric chloride, ferric sulfate or ferric carbonate.

The cross-sectional size of the window, reported as a window width ($W_w$) reported herein as a diameter of a circle with the same cross-sectional area or equivalent diameter, is preferably sufficiently small to allow the sample to remain in the window by surface tension yet sufficiently wide to allow the light to pass there through without obstruction by the body. The coupon width ($W_c$), reported herein as a diameter of a circle with the same cross-sectional area or equivalent diameter, is limited between the bounds of being large enough to reversibly absorb sufficient reagent therein to ensure all analyte is reacted or that the reaction between the analyte and reagent is not reagent limited. A coupon which is as small as possible may be advantageous in some embodiments, such as for small liquid sample sizes. It is preferred that the window width be at least 0.1 mm to no more than 10 mm, and more preferably at least 1 mm to no more than 5 mm. It is preferred that the coupon width be at least 1 mm to no more than 20 mm and more preferably at least 2 mm to no more than 10 mm.

Figure 3:
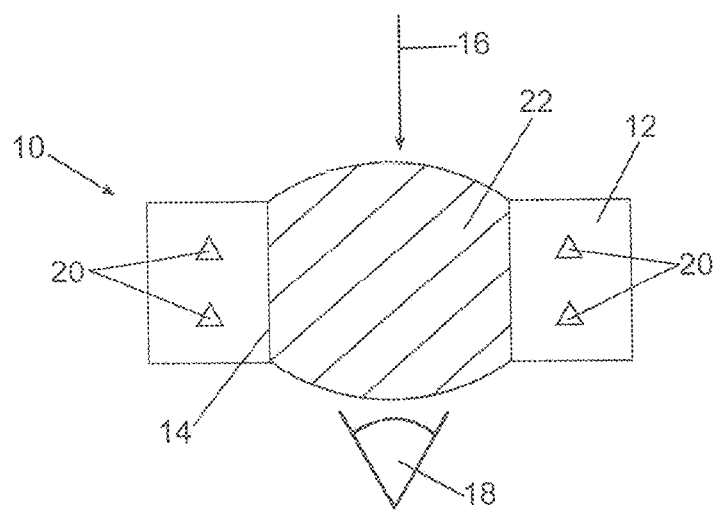
FIG. 3 is a schematic representation of an embodiment of the invention.

An embodiment is illustrated in cross-sectional schematic view in FIG. 3. In FIG. 3 a coupon, 10, comprises a sample, 22, within the window wherein the sample has a color intensity correlated to the reacted analyte concentration. The column of liquid remains in the window by a combination of capillary action and surface tension. For transmission spectroscopy, the light, 16, passes through the sample, to be received by the detector, 18, as attenuated light wavelength specific wherein the attenuation is correlated to the amount of reacted analyte in the window. For reflectance spectroscopy, the detector can be placed on the same side of the coupon as the light source. A transparent plate can be used to seal one or both sides of the window.

Figure 5:
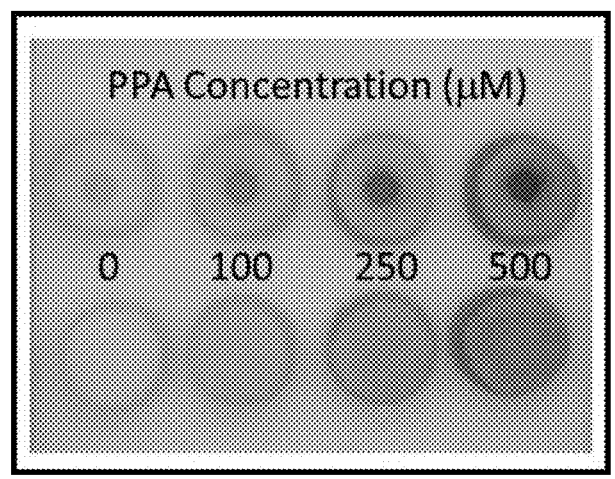
FIG. 5 is a photographic image of an embodiment of the invention.

FIG. 5 shows an example of this coupon design for analysis of PPA concentration in simulated urine for coupons with and without a central window (all other conditions being identical). These coupons are made from 2.45 mm thick blotting filter paper with 10 mm outer diameter. The central window in the coupons is formed using a simple 3-mm hole punch. As clearly evident, the intensity of color change is proportional to the concentration of PPA in the test fluid for both types of coupon, but the color change is much more intense and much more uniformly presented in the column of fluid held within the coupon with the window compared to the coupon without the window. Though not limited thereto, a cylindrical body is preferred due to the consistent distance across the window and therefore minimization of diffusion gradients of the reactant into the sample.

The cylinder body is formed from a material capable of absorbing, and releasing, the reactants. While not limited thereto, cellulose based materials, such as paper, are particularly suitable for demonstration of the invention due to the suitability, wide availability and cost. Filter papers are particularly suitable for demonstration of the invention. The coupons can also be made of materials that are translucent or opaque such to transmit light, not transmit light, or transmit light to a limited degree.

Another embodiment of this invention could be a sheet of material with holes punched through. The whole sheet could be impregnated with the color indicating reagent. As another example, a whole sheet of absorbent material could be used with impermeable divisions that isolate subsections of the sheet, with each subsection having a different color-indicating compound and each section having its own window for holding the column of liquid.

While described, for simplicity, with a single analyte and single reactant the invention can be utilized with multiple analytes to be sampled in the liquid and multiple reactants in the coupon. It would be apparent that the color intensity associated with each reacted analyte would be distinguishable from the other reacted analytes. Without limit thereto, in a particularly preferred embodiment would incorporate a reactant suitable for detection of PPA, such as ferric salts, and a reactant suitable for creatinine (CRE), wherein the reaction provides distinguishable color intensity.

The detector is any colorimetric sensor with sufficient sensitivity to measure the red-green-blue (RGB) absorbance color analysis for quantification or any other color-model including but not limited to HSV, HSL, and/or CMYK. Digital photography under controlled lighting conditions, is suitable for demonstration of the invention. The detector can be a photodiode or a camera comprising software sufficient to determine light intensity at a given wavelength or wavelengths. A microprocessor, either integral to a camera or as a distinct component, may be utilized for data collection and analysis. A conventional iPhone 5S is suitable for demonstration of the invention and capable of a measurement of PPA levels in urine down to as low as 5.0 µM which is 120× lower than the previous limitation for Phenistix strips. The intensity of red light, 400-700 nm, is suitable for measurement of the PPA level, however, other wavelengths can be used to augment the measurement or to measure additional reaction products.

An inherent problem with a urine test is the variability of the composition of urine caused by dilution effects due to the level of patient hydration. It is known that the renal clearance of creatinine is essentially invariant on an individual basis. Therefore, creatinine level can be used to normalize urine constituent concentrations that occur due to varying levels of patient hydration. For example, when normalized by creatinine, Phe levels in urine can be correlated to Phe levels in blood with the relationship between the two being sufficiently predictable enough for the urine analysis to be a sufficiently accurate representation of blood Phe levels. This relationship has a highly significant correlation between the ratio of mmole Phe/mol creatinine in urine and blood Phe levels over all concentrations when age was accounted for (i.e., 0-6 yrs. vs. >6 yrs), with correlation coefficients ranging from 0.89-0.93 for these two patient populations.

Similarly, because PPA is produced in the body in proportion to the Phe levels in blood, normalizing urine PPA concentration by urine creatinine concentration is similarly able to account for differences in patient hydration, thus enabling it to be used to estimate Phe levels in the blood stream. Colorimetric urine creatinine test strips are commercially available as AdultaCheck® test strips available from Sciteck Diagnostics and the chemical reaction employed in test strips can be employed as a parallel, or simultaneous, test for the instant invention. Alternatively, coupons with a central hole can be impregnated with any color-indicating reagents for creatinine to provide improved sensitivity and uniformity in the color change as compared to the AdultaCheck® test strips or the equivalent. Digital photography, controlled lighting, and RGB-scale readout can be used quantitatively to determine creatinine concentration in simulated urine samples spiked with known levels of creatinine over the physiological range of 0-400 mg/dL to demonstrate the invention.

The manner in which the lighting is controlled is not limited herein with the proviso that the lighting must be sufficient to not interfere with the results. White light can be used or a light with a specific wavelength range can be used. In one embodiment a monochromatic, or combination of monochromatic, lights can be employed.

The present invention has the potential to provide the PKU community a very simple, low-cost, noninvasive at-home method to enable daily monitoring of blood Phe levels as a supplement to regular blood testing. Not only would this method provide an extremely useful at-home test to help patients maintain blood Phe levels while awaiting blood test results, but its simple, low-cost, noninvasive features have the potential to enhance patient compliance particularly for the non-maternal adult patient population, which has a tendency to forgo routine blood testing and clinical visitations as they get older.

Figure 4:
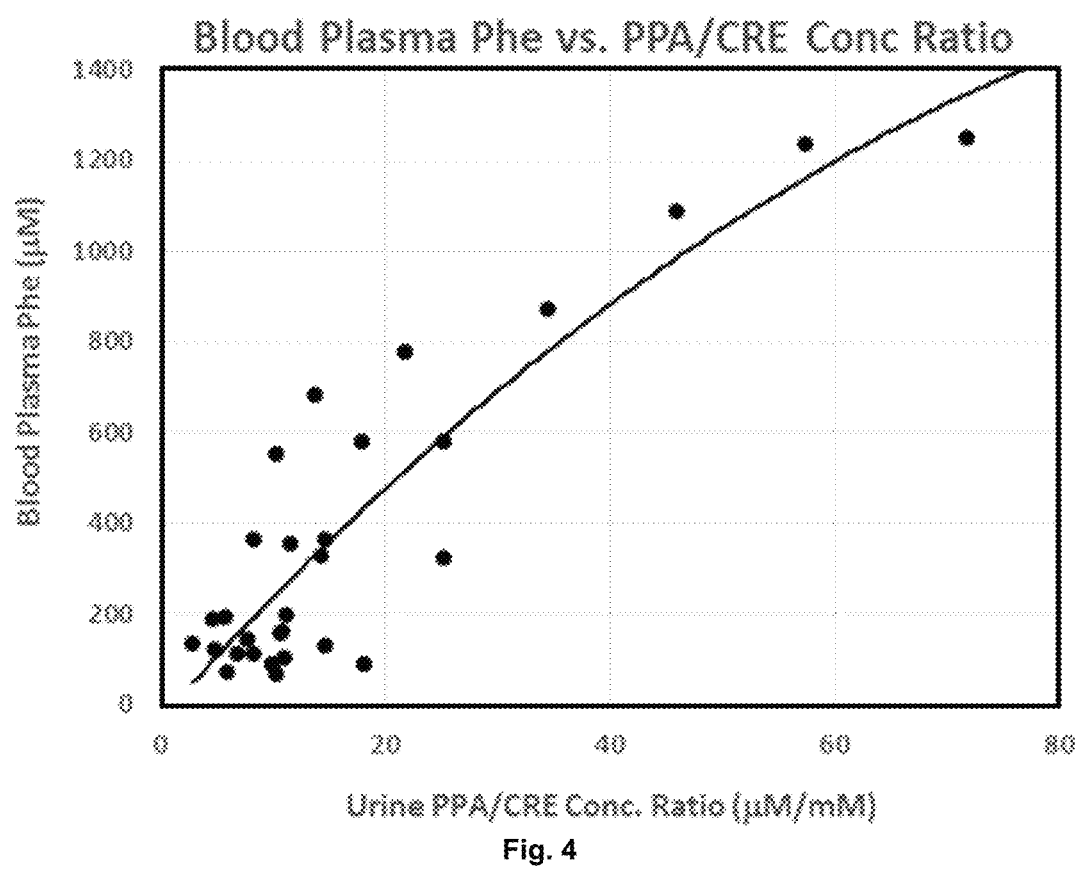
FIG. 4 is a graphical representation illustrating an embodiment of the invention.

The present invention could utilize the Phenistix formula test by redesign of the test with a novel substrate, using a light-controlled environment for color determination, using a smartphone to obtain a digital photograph of the test samples, and an RGB color app, such as ColorHelper, to provide a quantitative measure of the color intensity of the samples. In one embodiment the coupon could comprise a thick and highly absorbent white-paper-towel-based substrate wrapped in Parafilm M® approximately 8 mm in diameter and 4 mm thick, which would be found to provide color intensity as strong as in pure liquid samples. The test coupons could be soaked in Phenistix formula and then dried. The Phenistix formula based on the composition described in U.S. Pat. No. 3,048,475 which is incorporated herein by reference could be used wherein the formulation comprises 20 mL of ethanol, 80 mL nanopure water, 5.8 grams ferric ammonium sulfate, 8.9 grams magnesium sulfate and 6.5 grams of N-cyclohexylsulfamic acid. A simulated urine composition composed of urea and salts dissolved in nanopure water suitable for demonstration of the invention would comprise 13.4 grams of urea, 8.00 grams of NaCl, 2.61 grams of potassium sulfate, 1.64 grams of potassium chloride, 0.78 grams of magnesium sulfate, 0.23 grams of potassium bicarbonate, 0.23 grams of potassium phosphate, 0.14 grams of magnesium carbonate and 0.06 grams of calcium phosphate dissolved in 1.0 L of water. Phenylpyruvic acid (PPA) could be added to the simulated urine samples at concentrations of 0, 5,10, 50, 100, 250, 500 µM to demonstrate the invention. The test substrates could be dipped in the simulated urine samples and placed on a white background sample tray and positioned inside a light-controlled enclosure. The inside of the enclosure could be lit by white light emitting diodes (LEDs), such as those available from SopoTek, with internal baffling to provide diffuse lighting conditions for the samples and to prevent glare. The light-box enclosure could have a small opening at the top to allow a photograph to be taken of the enclosed samples. A smartphone could be used to take digital photographs of the samples one minute after exposure to the simulated urine, with an RGB color app used to provide quantitative RGB values for each sample between 0-255 each for R, G, and B. Similar testing would be conducted using the simulated urine spiked with creatinine over the range of 0-200 mg/dL (0-18 mM) with color change indicated using Adulta-Check® 4 creatinine test strips available from Sciteck Diagnostics. Representative calibration plots for red (R) color intensity for PPA and CRE, the most strongly indicating color, are presented in FIG. 4. FIG. 4 graphically illustrates the expected results using colorimetric coupons for the measurement of phenylpyruvic acid (PPA) and creatinine concentration in urine samples for individuals with PKU with a ratio of urine PPA/CRE concentration plotted against blood plasma phenylalanine (Phe) concentration. The coefficient of determination for the best-fit polynomial line to the data set would be expected to be calculated as R=0.9011. For PPA and CRE levels higher than 500 µM and 200 mg/dL, respectively, urine samples could be diluted with water, such as 5× dilution, to shift their R absorbance values to lie within the respective calibration plot. Alternatively, calibration plots for PPA and CRE could be created for simulated urine spiked over a higher range of concentration of PPA and CRE. In practice analyte concentrations of at least 1 µM to less than 50 mM can be measured.

Urine creatinine measurement is preferably done using alkaline picric acid, picric acid in solution with sodium hydroxide, which reacts with creatinine to form a colored product via the Jaffe reaction. The concentration of this product can then be measured using spectrophotometry. By comparing the absorbance of a standard with a known creatinine concentration to the absorbance of a patient's urine sample, the creatinine concentration in the patient's urine can be calculated.

The comparative phenylalanine concentration in dried blood spots could be measured using stable isotope dilution tandem mass spectrometry (MS/MS) wherein a 3 mm punch from a dried blood spot mixed with a solvent solution containing stable isotope-labeled internal standards of various amino acids. Blood from the spot would be eluted during a 30 minute incubation in an orbital shaker. The filter paper would be removed and the eluate dried under nitrogen. Organic solvent would be added and the mixture injected into a Quattro Micro MS/MS system. Quantification would be performed by comparing the area of the phenylalanine to the area of the stable isotope label.

These measured values shown in FIG. 4 could then be entered into a smartphone app that would predict a corresponding blood Phe level from a new urine test based on the ratio of PPA/CRE concentrations. Devices could be employed which plot urine PPA/CRE vs. DBS blood Phe values over time and the values and the correlation between these two metrics could be continually updated on a dynamic basis. This capability would then automatically adjust for changes in an individual PKU patient as they grow older. Wireless communication capability could also be incorporated within the app to transmit the patient's predicted values to a designated clinical facility for improved patient monitoring.

The invention has been described with reference to the preferred embodiments without limit thereto. One of skill in the art would realize additional embodiments and alterations which are not specifically set forth but which are within the scope of the invention as more specifically set forth in the claims appended hereto.

The invention claimed is:

1. A system for monitoring an analyte concentration in liquid comprising:
   a coupon comprising an absorbent body, which is translucent or opaque such to transmit light, not transmit light, or to transmit light to a limited degree, with a window through said absorbent body wherein said liquid is maintained in said window by capillary action and surface tension;
   a reactant in said absorbent body wherein said reactant is capable of reacting with a designated analyte to induce a color change in proportion to the concentration of the analyte, with the reactant diffusing into said window to react with an analyte in said liquid, or with the reactant reacting with the analyte within the absorbent body itself, with the color-indicating by-product of this reaction diffusing into said window induce a color change in the contained liquid, wherein said analyte is present in said analyte concentration to form a reactant with a color wherein said color has an intensity which correlates to said analyte concentration; and
   a light source capable of passing light into said window wherein said light is attenuated by said color proportional to said analyte concentration to form attenuated light further comprising a system capable of measuring an intensity of said attenuated light.

2. The system for monitoring an analyte in liquid of claim 1, wherein said intensity measurement is by a device selected from the group consisting of a color-sensing instrument, a light-sensing instrument and a human eye.

3. The system for monitoring an analyte in liquid of claim 2 further comprising a color chart comprising a color correlated to a concentration of said analyte.

4. The system for monitoring an analyte in liquid of claim 1 wherein said liquid is urine.

5. The system for monitoring an analyte in liquid of claim 1 wherein said analyte is phenylpyruvic acid.

6. The system for monitoring an analyte in liquid of claim 1 wherein said reactant is a ferric salt.

7. The system for monitoring an analyte in liquid of claim 6 wherein said ferric salt is selected from ferric ammonium sulfate, ferric chloride, ferric sulfate and ferric carbonate.

8. The system for monitoring an analyte in liquid of claim 1 wherein said liquid further comprises creatinine in a creatinine concentration.

9. The system for monitoring an analyte in liquid of claim 8 further comprising a device for measuring said creatinine concentration.

10. The system for monitoring an analyte in liquid of claim 9 further comprising a device for correlating said creatinine concentration to said analyte concentration.

11. The system for monitoring an analyte in liquid of claim 9 wherein said device comprises a second coupon.

12. The system for monitoring an analyte in liquid of claim 1 wherein said light source comprises red light.

13. The system for monitoring an analyte in liquid of claim 1 wherein said detector detects red light.

14. The system for monitoring an analyte in liquid of claim 1 wherein said light source comprises color other than red or multiple colors.

15. The system for monitoring an analyte in liquid of claim 1 wherein said detector detects color other than red or multiple colors.

16. The system for monitoring an analyte in liquid of claim 1 wherein the color is determined by eye.

17. The system for monitoring an analyte in liquid of claim 16 comprising comparing said color to a control color on a chart wherein said control color is correlated to said analyte concentration.

18. The system for monitoring an analyte in liquid of claim 1 wherein said analyte concentration is less than 50 mM.

19. The system for monitoring an analyte in liquid of claim 16 wherein said analyte concentration is at least 1 µM.

* * * * *